United States Patent [19]
Tanaka et al.

[11] Patent Number: 6,166,225
[45] Date of Patent: Dec. 26, 2000

[54] PROCESSES FOR PRODUCING DIALDEHYDE MONOACETALS

[75] Inventors: Yasutaka Tanaka, Ohtake; Hiroaki Uenakai, Kakogawa; Giichi Shimada, Hiroshima, all of Japan

[73] Assignee: Daicel Chemical Industries, Ltd., Osaka, Japan

[21] Appl. No.: 09/403,215

[22] PCT Filed: Feb. 17, 1999

[86] PCT No.: PCT/JP99/00692

§ 371 Date: Oct. 15, 1999

§ 102(e) Date: Oct. 15, 1999

[87] PCT Pub. No.: WO99/41249

PCT Pub. Date: Aug. 19, 1999

[30]        Foreign Application Priority Data

Feb. 17, 1998  [JP]  Japan .................................. 10-050008
Feb. 17, 1998  [JP]  Japan .................................. 10-050009
Jul. 23, 1998  [JP]  Japan .................................. 10-223713

[51] Int. Cl.$^7$ ................................................ C07D 321/00
[52] U.S. Cl. ............................................................ 549/347
[58] Field of Search .............................................. 549/347

*Primary Examiner*—Amelia Owens
*Attorney, Agent, or Firm*—Morgan & Finnegan, L.L.P.

[57]           ABSTRACT

In a method of producing a dialdehyde monoacetal(s) (III) from dialdehyde(s) (I) and diol(s) (II), the present invention provides a method comprising a first step wherein said dialdehyde(s) (I) and said diol(s) (II) are reacted to produce dialdehyde bisacetal(s) (IV), the amount by mole of said diol(s) (II) being at least twice the amount by mole of said dialdehyde (I) and a second step wherein said dialdehyde bisacetal(s) (IV) is reacted with said dialdehyde (I). The present invention also provides a method of producing a glutaraldehyde monoacetal via reacting 2-Y-3, 4-dihydro-2H-pyran or a ring-substituted derivative thereof with diol. This method comprises a second step reaction wherein glutaraldehyde (iv) which is one of the by-products of the first step reaction is reacted with glutaraldehyde bisacetal (v) which is another by-product of said first reaction. According to the present invention, in the above-mentioned method of producing a glutaraldehyde monoacetal (iii), after the end of the first step reaction, the crude reaction solution is heated at a temperature of from 100° C. to 200° C. to produce the glutaraldehyde monoacetal (iii) from the by-products, low boiling-point components produced from the substituant group Y being removed via distillation.

10 Claims, No Drawings

PROCESSES FOR PRODUCING DIALDEHYDE MONOACETALS

TECHNICAL FIELD

A first aspect of the present invention relates to a method of preparing dialdehyde monoacetals. More particularly, the present invention relates to a method consisting of two steps instead of a direct method which consists of directly producing a dialdehyde monoacetal from a dialdehyde and a diol. According to the method of the present invention, in a first step, dialdehyde bisacetal (which is an intermediate) is firstly obtained and in a second step, this dialdehyde bisacetal obtained is used to produce a dialdehyde monoacetal.

A second aspect of the present invention relates to a high production-yield method for preparing glutaraldehyde monoacetal (GADMA) from a specific pyran and a diol. In more detail, the second aspect of the present invention relates to a method of preparing GADMA in a high yield by using reactions between by-products of the reaction in addition to the reaction of a specific pyran with a specific diol.

A third aspect of the reaction relates to a method for improving the yield in the method of the second aspect of the invention by specifically determining conditions for the distillation of GADMA.

The compounds in the first aspect of the invention will be abbreviated as follows using the numbers of the General Formulae.

(I) dialdehyde;
(II) diol;
(III) dialdehyde monoacetal;
(IV) dialdehyde bisacetal.

These compounds are also used in the second and third aspect and referred to the numbers and abbreviations of their General Formulae as in the first aspect of the invention.

Regarding the second and the third aspects of the present invention, the compounds used are abbreviated as follows according to the numbers of their General Formulae.

(i) 2-Y-3, 4-dihydro-2H-pyran: YDP; 2-methoxy-3, 4-dihydro-2H-pyran: MDP;
(ii) diol ethylene glycol: EG;
(iii) glutaraldehyde monoacetal: GADMA
(iv) glutaraldehyde: GA;
(v) 2, 2'-trimethylbis (1, 3-dioxolane)(corresponding to a glutaraldehyde bisacetal which is a glutaraldehyde whose terminal formyl groups are both converted in acetal groups): GADBA;

The acetal compounds formed from the alcohol corresponding to the Y of the above-mentioned YDP and glutaraldehydes are referred as Y acetals.

TECHNICAL BACKGROUND

In general, dialdehyde monoacetals have formyl groups which can be easily converted into an amino group, a hydroxyl group, a carboxyl group or an aminocarboxyl group; on the other hand, their acetal group is extremely stable in neutral or basic conditions but can be easily converted into formyl group under acidic conditions. Consequently, using such characteristics, the two terminal groups of the dialdehyde can be easily converted into two different groups and each kind of these compounds is very important since they are very useful as intermediates for synthesis particularly for synthesis of medical, pharmaceutical and agricultural compounds.

Among them, GADMA which is a typical compound of the above-mentioned dialdehyde monoacetal is particularly considered as important.

Heretofore, several methods have been proposed in the prior art as industrial methods of preparing a dialdehyde monoacetal. However, it is preferred that starting materials can be economically and readily obtained as industrial chemical products which are commercially supplied. Accordingly, it has been thought to be advantageous to directly prepare a dialdehyde monoacetal via the reaction of a dialdehyde with a diol.

An example of this direct method is shown by the following reaction formula in which GA which is used as a dialdehyde and EG used as a diol are used to produce GADMA.

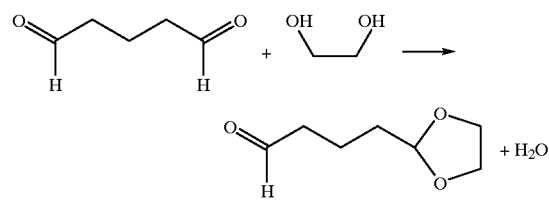

According to this reaction scheme, it seems that GADMA is readily produced. However, practically, it is difficult to obtain GADMA in high yield. The reason is that the above-mentioned reaction is an equilibrium reaction and, moreover, there is a chemical equilibrium system between GADMA and the following GADBA which are by-products, at the same time.

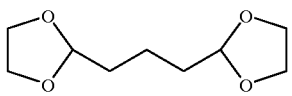

Consequently, as far as the above-mentioned reaction method is used, there will be some trouble regarding the isolation of GADMA via distillation of a reaction mixture containing the five following components GA, GADMA, GADBA, EG and water. Moreover, during distillation, low-boiling point compounds such as water are usually removed from the system and consequently, there is an increase of GADBA. For this reason, the yield of the target GADMA is of only 20% maximum with respect to the GA which is a starting material. This is thus a problem. These facts will be further explained on the basis of Comparative Example I-1 described later on.

In a reaction process using the reaction between GA and EG and a catalyst, regarding the synthesis reaction of GADBA via a distillation process, even if the acid catalyst can be removed via separation (in the case where a solid catalyst has been used) or via neutralization (in the case where a catalyst forming a homogenous system has been used), the synthesis reaction of GADBA cannot be completely avoided. This matter will be made clear on the basis of Comparative Example I-1.

JP-B-76004211 proposes as a method for avoiding the synthesis reaction of GADBA during distillation process, to add dropwise a small amount of EG in an excess of GA and in the same time to remove the synthesized water from the reaction system. However, according to this method, the speed of the synthesis of GADBA is higher than the speed of the synthesis of GADMA which is a desired product and thus, this method requires a very precise control under extremely restricted conditions to control the synthesis of GADBA at a suitable speed while removing water. This method is thus very difficult to use industrially.

Further, a method for the industrial preparation of GADMA via a reaction between 2-alkoxy-3, 4-dihydro-2H-pyran and a diol has also been disclosed. This method is also used as an industrial method for the preparation of GADMA (JP-A-49035383). However, the inventors of the present invention have carried out further investigations and experiments to synthesize GADMA on the basis of the method described in the above-mentioned patent publication and have understood that the yield per mole of the GADMA which can be obtained by this method cannot be more than 13% or so (confer comparative Example III-1 of specification of the present invention) with respect of the moles of the starting materiel 2-alkoxy-3, 4-dihydro-2H-pyran. They have also understood that this yield is not industrially sufficient at all.

Moreover, it is explained in the Examples of the former JP-A-49035383 that the yield of the by-produced GADBA is 26% and that GADBA can be easily converted into GADMA by reacting with water. However, according to the investigations of the inventors of the present invention, the reaction between GADBA and water effectively produces GADMA and diol but when trying to isolate by distillation GADMA from the reaction mixture, water is distilled out of the system and consequently the GADMA synthesized are converted into GADBA via the reverse reaction with diol. For this reason, isolation of GADMA as an industrial product is clearly impossible. This matter is clearly proved in Comparative Example II-1 of the present description.

Thus, it has to be noticed that the synthesis method of GADMA from by-product GADBA as proposed in the previous document JP-A-49035383 is difficult to be used in practice.

The first problem of the present invention is to find out a method of producing dialdehyde monoacetals in high yield which are useful as intermediate products for producing medicines, agricultural chemicals or the like, using dialdehydes and diols as starting materials.

The second and third problems of the invention are to find out a method which enables producing at a high yield GADMA by reacting YDP compounds such as 2-alkoxy-3, 4-dihydro-2H-pyran or their ring-substituted derivatives and diols.

As a result of intense investigations for resolving the first problem mentioned above, it has been found out that the most sure method of producing dialdehyde monoacetals is a two-steps method; the first step of this method is the synthesis of almost pure aldehyde bisacetal via adding in a system containing dialdehyde more than twice by mole of diol with respect to one mole of dialdehyde, reacting such a system and then removing by distillation the excess amount of diol and the produced water; the second step consists of obtaining dialdehyde monoacetal via reacting the dialdehyde bisacetal obtained with dialdehyde which is a starting material and then removing by distillation produced water and the excess amount of diol.

Further, as a result of intense investigations for solving the second and third problems of the present invention, the inventors found that it is possible to nearly completely isolate GADMA without any problems regarding the reverse conversion of GADMA into GADBA which occurs during isolation of GADMA. This can be obtained via using a method consisting of a first step wherein GADMA can be obtained via reacting 2-alkoxy-3, 4-dihydro-2H-pyran and diol, and then by reacting GA with another by-product of the former reaction without hydrolysis of the first by-product due to water addition.

Further, the present inventors have discovered how to produce and isolate at a high yield GADMA via keeping the temperature of the solution in the bottom of the distillation column in a determined range during an initial distillation operation of the distillation for isolating GADMA.

DISCLOSURE OF THE PRESENT INVENTION

The first aspect of the present invention is as described in points 1 to 3.

In a method for producing dialdehyde monoacetal (III) from dialdehyde (I) and diol (II), the present invention provides, according to a first point, a method wherein a dialdehyde bisacetal (IV) is obtained according to a first step via reacting the dialdehyde (I) and more than twice by mole of the diol (II) and according to a second step this dialdehyde bisacetal (IV) is reacted with a specific dialdehyde (I) to produce a specific dialdehyde monoacetal.

(wherein $R^1$ is a hydrocarbon group)

(wherein $R^2$ is a hydrocarbon group)

(wherein $R^1$ and $R^2$ are the same as in Formulae (I) and (II)

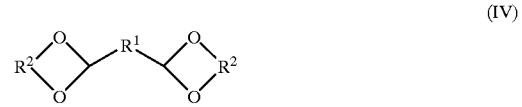

(wherein $R^1$ and $R^2$ are respectively the same as defined in Formulae (I) and (II))

According to a second point, the present invention provides a method for producing dialdehyde monoacetal according to the above-mentioned first point wherein the first and/or the second step of the reaction are carried out in the presence of an acidic catalyst.

According to a third point of the present invention, dialdehyde(s) used is made anhydrous via using the reaction thereof with dialdehyde bisacetal(s) (IV).

The second and third aspects of the invention will be described in the following points 4 to 10.

According to the fourth point, the present invention provides a method for producing a glutaraldehyde monoacetal via reacting a 2-Y-3, 4-dihydro-2H-pyran or a derivative thereof as shown in General Formula (i) with a diol as shown in General Formula (ii) to obtain a glutaraldehyde monoacetal as shown in General Formula (iii), characterised in that said glutaraldehyde monoacetal (iii) is produced via a second step reaction wherein said glutaraldehyde (iv) which is a by-product of the first step reaction is reacted with glutaraldehyde bisacetal (v) which is another by-product of the same reaction; 2-Y-3, 4-dihydro-2H-pyran, diol (ii), glutaraldehyde monoacetal (iii), glutaraldehyde (iv) and glutaraldehyde bisacetal (v) are as shown in the following General Formulae:

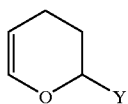

(i)

(wherein Y is a hydroxy group, an alkoxy group, an aryloxy group or an aralkyloxy group)

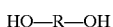

(ii)

(wherein R is a divalent saturated or unsaturated hydrocarbon group having from 1 to 10 carbon atoms)

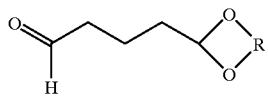

(iii)

(wherein R is the same as defined in General Formula (ii))

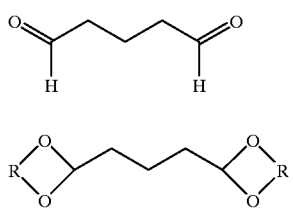

(iv)

(v)

(wherein R is the same as defined in General Formula (ii))

According to a fifth point, the present invention provides a method of producing a glutaraldehyde monoacetal according to the fourth point, wherein in the process for isolating the glutaraldehyde monoacetal via distillation of the crude reaction solution in the first step, an initial distillation operation for removing low boiling-point components is carried out while maintaining the temperature of the solution of the bottom of the distillation column in the range of 100° C. to 200° C.

According to a sixth point, the present invention provides the method of producing a glutaraldehyde monoacetal according to the fourth point, wherein after the completion of the first step reaction, the crude solution is heated until a temperature between 100° C. and 200° C. and the glutaraldehyde monoacetal (iii) is produced from by-products, and then low boiling-point components produced from the substituant group Y being distilled out during the synthesis of said glutaraldehyde monoacetal (iii).

According to a seventh point, the present invention provides a method of producing a glutaraldehyde monoacetal according to the fourth point, wherein said 2-Y-3, 4-dihydro-2H-pyran is 2-methoxy-3, 4-dihydro-2H-pyran and said diol is ethylene glycol.

According to an eighth point, the present invention provides the method for producing a glutaraldehyde monoacetal according to the seventh point, wherein a separation via distillation into the fraction primarily containing glutaraldehyde and the fraction primarily containing glutaraldehyde monoacetal is carried out.

According to a ninth point, the present invention provides the method for producing a glutaraldehyde monoacetal according to the eighth point, wherein the separation of the fraction primarily containing glutaraldehyde is carried out while the temperature of the solution of the bottom of the distillation column is ranging from 130° C. to 142° C., the pressure of the top of the distillation column being ranging from 25 to 35 torr and the temperature of the top of the distillation column being ranging from 95° C. to 119° C.

According to a tenth point, the present invention provides method for producing a glutaraldehyde monoacetal according to the eighth point or the ninth point, wherein the separation of the fraction primarily containing glutaraldehyde monoacetal is carried out while the temperature of the solution of the bottom of the column is ranging from 142° C. to 168° C. and the pressure of the top of the column ranging from 25 torr to 35 torr and the temperature of the top of the column being ranging from 119° C. to 124° C.

BEST MODE TO CARRY OUT THE INVENTION

The first aspect of the invention will be now described.

Aldehydes (I) that can be practically used in the first aspect of the present invention are, for example, glutaraldehyde, malonic dialdehyde, succinic dialdehyde, P-methylglutaraldehyde, adipic dialdehyde, maleic dialdehyde, phthalic dialdehyde or other aliphatic and aromatic dialdehydes.

Further, these dialdehydes which generally do not contain water and have a high degree of purity easily form oligomers or polymers and thus it is difficult to store them for a long time. Commercially supplied products are an aqueous solution containing generally not less than 50% by weight of water.

The presence of water in dialdehyde (I) does not involve any problem in the synthesis of dialdehyde bisacetal by reaction with diol (II) according to the first step of the first aspect, of the invention (hereinafter referred as first step of the first aspect). However, the dialdehyde is preferably essentially anhydrous as in the second step (hereinafter, referred as second step of the first aspect) of the first aspect of the invention. In the reaction between the dialdehyde bisacetal (IV) and the dialdehyde (I) in the second step of first aspect the synthesis of the dialdehyde monoacetal (III) is obstructed in a chemical equilibrium. The water contained in dialdehyde (I) is thus preferably removed as soon as possible before the reaction with the diol (II).

Molecular sieves, calcium sulphate or other dessicant agents are preferably used for removing water. However, sodium, calcined lime or other dessicant agents having a basic group cannot be used because they allow the dialdehydes to polymerize. Water can be removed using specific dessicant agents but generally, distillation is used because it is economically interesting.

The dialdehyde (I) from which water has been removed is thus anhydrous and has a high purity. Such a dialdehyde (I) has a tendency to polymerize and solidify as explained above. However solidification progresses very slowly and usually aldehyde can be stored as a liquid for several days. Thus, if the dialdehyde (I) is mixed with other starting materials such as the dialdehyde bisacetal (IV) before solidification, it does not polymerize and can be always treated as a liquid. It can be used industrially without any specific problem.

Specifically, examples of diols (II) to be used in the present invention are, for example, ethylene glycol (EG), 1, 2-propylene glycol (PG), 1, 3-propylene glycol, 1, 3-butanediol, 1, 4-butanediol, catechol or other aliphatic, aromatic diols. Among them, EG and PG are preferably used because they have a boiling point enabling an easy separation via distillation from the target product, they are also inexpensive and easy to provide, easy to convert in acetal and they can be easily converted into formyl groups.

Further, the synthesis method of the dialdehyde bisacetal (IV) which acts as a synthesis intermediate in the present invention will be now explained. The dialdehyde bisacetal (IV) is synthesized from the dialdehyde (I) and the diol (II). The dialdehyde (I) is generally commercially supplied as an aqueous solution as explained above. The synthesis of the dialdehyde bisacetal (IV) of the first step of the first aspect of the present invention can be carried out in an aqueous solution without any problem.

The water contained in the dialdehyde which is used in the second step of the first aspect of the invention will be explained later.

It is to be noted that although the reaction of the first step of the first aspect of the invention is generally carried out without any solvent, optionally, hexane, heptane, toluene or other organic solvents may be used.

In the reaction of the first step of the first aspect of the present invention, the molar ratio of the diol (II) with respect to the added dialdehyde (I) is stoichiometrically equal to 1:2. However, considering that the reaction is an equilibrium, the molar ratio of the diol (II) is preferably more than 2. Usually, this molar ratio is from 2.1 to 4.0 and preferably from 2.2 to 3.0. When it is less than 2.1, the conversion into the dialdehyde bisacetal (IV) is occasionally insufficient. On the other hand, when it is more than 4.0, the yield of the dialdehyde bisacetal (IV) is not improved or the amount of the diol (II) to be removed via distillation is increased whereby requiring an increased energy. Considering these points, the diol is preferably provided in a molar ratio ranging from 2.2 to 3.0.

Further, the reaction of the first step of the first aspect of the invention can be carried out even without any catalysts. However, since an efficient reaction speed cannot be obtained, a catalyst is preferably used for industrial scale.

Sulphuric acid, hydrochloric acid, phosphoric acid, acetic acid, paratoluenesulphonic acid, methanesulphonic acid or other generally used acids, a variety of cationic ion-exchange resins, silica alumina, zeolites, activated white-earth or other solid acids can also be used. Among them, cationic ion-exchange resins of the sulphonic acid-type are particularly suitable because of their suitable acidity and their easy treatment after reaction.

Regarding the amount of catalyst used, this amount depends on the kind of acid used. However, usually, when a sulphonic acid-type cationic ion-exchange resin is used, the amount of catalyst used is, for example, in the range of 0.1 to 10% by weight of the reaction solution. When this amount is less than 0.1% by weight, a sufficient reaction speed cannot be obtained in numerous cases. On the other hand, when the amount is more than 10% by weight, the separation of the catalyst is cumbersome and thus catalyst is preferably used in an amount of less than 10% by weight.

The temperature of the first step reaction of the first aspect of the invention is usually from 20° C. to 200° C., preferably from 30° C. to 150° C. When the temperature is less than 20° C., in several cases a sufficient reaction speed cannot be obtained. On the other hand, when the temperature is more than 200° C., the amount of polymers or other by-products tends to increase.

The first step reaction of the first aspect of the invention may be a batch type reaction, a semi-batch type reaction or a continuous reaction. Further, when a solid catalyst is used in this reaction system, in addition to a reaction style in which the catalyst is suspended in starting materials under stirring a reaction style can be also used in which the starting materials are passed through a catalyst bed or passed therethrough while recirculating.

Moreover, since water, which is produced by the conversion of the dialdehyde (I) into the dialdehyde bisacetal (IV), is removed from the reaction system during the reaction, a reaction distillation can be used. Instead of this method, water can be removed by distillation in a different apparatus. However, in such a case, since the reaction of conversion of dialdehyde (I) into dialdehyde bisacetal (IV) progresses in the solution of the bottom of the distillation column during distillation and due to water removal via distillation, the reaction results in carrying out according to the above-mentioned reaction distillation even though not being intended.

Consequently, after reaction, catalyst is separated from the reaction solution and the reaction solution is neutralized. Although it may be considered that a distillation is disadvantageous when using a solid catalyst, even if it has to be removed by filtration due to installation restrictions, as explained above, the reaction proceeds at a reduced speed during distillation. For this reason, there is no problem in carrying out an usual batch distillation for several hours. However, an acid catalyst is preferably remained in the system when the residence time of liquid is short in a process for carrying out a continuous distillation.

When a distillation is carried out after reaction, water, the diol (II) and the dialdehyde bisacetal (IV) can be separated respectively in appropriate conditions. However, when there is no need to recycle the diol (II), the diol (II) and water may be discharged without separation. Further, the dialdehyde bisacetal (IV) does not need to be distilled out and isolated, and it can be used in a next reaction in a form of a liquid discharged from bottom.

In the second step of the first aspect of the invention the dialdehyde bisacetal (IV) obtained is reacted with dialdehyde (I) which is a starting material. However, it is different from the use of the dialdehyde (I) in the first step of the first aspect of the present invention. In this reaction, water which is present in the dialdehyde (I) reacts with the dialdehyde bisacetal (IV) which coexists in the system. Due to this reaction, diol (II) is separated. As a result, in the distillation process, the reaction between the dialdehyde monoacetal (III) and the diol (II) finally occurs and consequently the yield of the dialdehyde monoacetal (III) is reduced. Consequently, regarding the yield of the dialdehyde monoacetal (III), the lower the water concentration is, the better it is.

Dialdehyde (I) used in the present invention has a boiling point higher than water and for this reason during distillation after removing water as a low boiling point product out of the system, the dialdehyde (I) can be easily recovered as the solution of the bottom of the column.

The concentration of water remaining in dialdehyde (I) is preferably lower as explained before. This dialdehyde (I) is not necessarily anhydrous but its water content is preferably lower than or equal to 10% by weight. However, the water content of dialdehyde (I) is preferably less than few % by weight so that it can be used without any problem in the reaction of the second step of the first aspect of the invention.

Further, the purity of dialdehyde (I) after removing water has to be taken into consideration. As explained hereinabove, the dialdehyde (I) having a high purity polymerizes and solidifies. Oligomers and polymers of dialdehyde (I) react as the corresponding monomer itself with the dialdehyde bisacetal (IV) to give the dialdehyde monoacetal (III). This reaction is not a problem. However, when it is once solidified, there are handling problems. Fortunately, usually polymerisation of the dialdehyde (I) is very slow and it can be stored for several days as a liquid and consequently the above-mentioned handling problem can be avoided by mixing in advance dialdehyde (I) from which water has been removed and dialdehyde bisacetal which becomes rapidly its reaction partner in the reaction of the second step.

Conditions of the reaction between the dialdehyde (I) and the dialdehyde bisacetal (IV) which is the reaction of the second step of the first aspect of the invention will be now described.

The molar ratio of the dialdehyde (I) with respect to the dialdehyde bisacetal (IV) introduced into the reaction vessel is theoretically the most efficient for the synthesis of dialdehyde monoacetal when near 1.0. However, when a reaction distillation method is carried out in batch, the dialdehyde bisacetal (IV) is introduced in a surplus amount with respect to the dialdehyde (I) introduced for the first time reaction. After distilling out dialdehyde monoacetal (III), the dialdehyde (I) is added to the dialdehyde bisacetal which remains in the bottom of the column and the reaction is continued. Such a method is also efficient.

The reaction of the second step of the first aspect of the invention may usually be carried out without any solvent and catalyst but it possible to use the same solvents and catalysts as set in the first step reaction of the first aspect of the invention.

The amount of catalyst used, based on the amount of reaction solution is comprised in the same range as in the first step forth reaction of the first aspect of the invention.

The temperature of the second step reaction of the first aspect of the invention is in the same range as the temperature of the first step reaction of the first aspect of the invention.

The reaction type used for the second step reaction of the first aspect of the invention can be the same as those given in example for the first step reaction of the first aspect of the invention. Further, as explained in the first step of the first aspect of the invention, the reaction may be carried in the presence of a catalyst in the solution of the bottom of the distillation apparatus while the synthesised products are distilled out that is to say that a reaction distillation can be carried out.

Moreover, since the reaction which occurs at the second step of the first aspect of the invention is an equilibrium reaction, the dialdehyde (I) and the dialdehyde bisacetal (IV) which are introduced to react are not converted at 100% into dialdehyde monoacetal (III). However, needless to say that the dialdehyde (I) and the dialdehyde bisacetal (IV) which remain after the reaction can be again used as starting material for reaction.

As explained above, it is possible to produce the dialdehyde monoacetal (III) in an industrially sure and advantageous manner according to the first aspect of the present invention.

Hereinafter, the second and third aspects of the invention will be now explained.

At first explanations are based on the common part of the second and third aspect of the invention.

YDP which is a starting material for the present invention shown by the above-mentioned General Formula (i) is a 2H-pyran (or an α-pyran) intermediate; Y is an hydroxy group, an alkoxy group, an aryloxy group or an aralkyloxy group. Specifically, methoxy group, ethoxy group, propoxy group, butoxy group or the like can be given as examples of alkoxy groups; phenoxy group can be given as example of aryloxy group and benzyl group can be given as example of aralkyloxy. 2-methoxy-3, 4-dihydro-2H-pyran, 2-ethoxy-3, 4-dihydro-2H-pyran, 2-propoxy-3, 4-dihydro-2H-pyran, 2-butoxy-3, 4-dihydro-2H-pyran, 2-phenoxy-3, 4-dihydro-2H-pyran or the like can be given as specific examples of such compounds.

Further, in the present invention, ring-substituted derivatives of YDP (i) may also be used. One or more of the carbon atoms among the five carbon atoms of the pyran ring can have an alkyl group or an aryl group. As alkyl and aryl groups, groups corresponding to the alkoxy group and the aryloxy group of Y can be given as example.

Regarding YDP and its ring-substituted derivatives, when Y is an alkoxy group or the like, an alcoholic compound corresponding to the substituant group Y5 which is separated from the pyran ring by-produced according to the synthesis of GADMA which is a target product of the present invention. This by-produced alcoholic compound has usually to be separated from the target GADMA via distillation. For this reason, it has preferably a boiling point far from the boiling point of GADMA and preferably does not form an azeotropic compounds. Accordingly, substituant group Y is preferably a methoxy group, an ethoxy group, a propoxy group, a butoxy group or other alkoxy group corresponding to alcoholic compounds having a relatively low boiling point as compared to hydroxide group, aryloxy group or aralkyloxy group.

A linear chain alkylenediol can be used as the diol (ii) which is a starting material of the present invention shown by General Formula (ii). However, instead of the alkylene group, hydrocarbon group having a double bond, a triple bond, an aromatic ring in the molecule, or a functional group such as a side chain can also be suitably used.

Specifically, ethylene glycol (EG), 1, 2-propylene glycol (PG), 1, 3-propylene glycol, 1, 4-butanediol, 1, 3-butanediol, catechols or the like can be given as examples. Among them, EG and PG are preferably used because they are easy to separate via distillation from the synthesised products due to their boiling point, they are inexpensive and easy to provide, they are also easy to convert into acetal and they return easily to formyl group.

Hereinafter, the second aspect of the invention will be now mainly described.

The characteristics of the producing method related to the present invention are a first reaction between the YDP (i) and the diol (ii) to produce the GADMA (iii) (hereinafter designed as the first step of the second aspect) and then a reaction between the GA (iv) which are by-produced with the GADBA (v) to produce the GADMA (iii) (hereinafter designed as the second step of the second aspect).

First of all, the conditions of the reaction of the first step of the second aspect will be described.

The molar ratio of the diol (ii) based on the amount of the YDP (i) introduced for reaction is in a range of preferably 0.5 to 1.5. In this case, when the molar ratio is less than 0.5, the amount of GADMA produced has a tendency to be extremely low. On the other hand, when the molar ratio is more than 1.5, the amount of GADMA produced also decreased and at the same time, the amount of GADBA produced tends to increase, which is a by-product in which formyl groups at both terminals of glutaraldehyde are acetalyzed. As a result, operations for separating GADMA are complicated.

The reaction of the first step of the second aspect of the invention may usually be carried out without any solvent and the same solvents can be optionally used as those shown in the first step of the first aspect of the invention.

The reaction of the first step of the second aspect of the invention progresses without any catalyst but industrially, in order to sufficiently increase the reaction speed, it is possible to use an acidic catalyst. Catalysts that may be used are the same as those cited as examples in the first step reaction of the first aspect of the invention.

The amount of catalyst used, based on the amount of reaction solution is in the same range as in the first step reaction of the first aspect of the invention.

The temperature of the first step reaction of the second aspect of the invention is in the same range as the temperature of the first step reaction of the first aspect of the invention.

The reaction type used for the first step reaction of the second aspect of the invention can be the same as those given in example for the first step reaction of the first aspect of the invention Further, when Y is an alkoxy group, YDP (i) is converted into an acetal and a produced monovalent alcohol is extracted from the reaction system during the reaction. It is thus possible to use a reaction distillation.

After the reaction, in the case that a homogeneous catalyst is used, the catalyst is usually neutralised; in the case that a solid catalyst is used, it is separated from the reaction solution via filtration to give a crude reaction solution.

The GADMA (iii) which is the product is obtained from this crude solution reaction via distillation. In this distillation process, the GA (iv) which is also a by-product of the reaction and the GADBA (v) which is also a by-product is recovered as a low-boiling point component and as a high boiling-point component in the solution of the bottom of the distillation column, respectively.

There is exemplified a case that 2-methoxy-3, 4-dihydro-2H-pyran is used as the YDP, and ethylene glycol is used as diol. In this case, GA is separated via distillation from the crude reaction mixture and the product GADMA is preferably obtained according the following distillation conditions.

In the distillation of the crude solution, a main component in an initial fraction is methanol. When the temperature of the solution of the bottom of the column is equal to 130° C. for the initial fraction, the pressure of the top of the column is from 170 to 400 torr and the temperature thereof is from 35° to 56° C.

GA is obtained as a main component of the second initial fraction. In order to improve the yield of the product GADMA which is obtained via a main distillation, the temperature of the bottom of the column is preferably in the range of 130° C. to 142° C., the pressure of the top of the column is preferably in the range of 25 to 35 torr and the temperature thereof is preferably in the range of 95° C. to 119° C.

In the main distillation, in order to improve the yield thereof, the temperature of the bottom of the column is preferably from 142° C. to 168° C., the pressure of the top of the column is preferably in the range of 25 to 35 torr and the temperature of the top of the column is preferably in the range of 119° C. to 124° C.

Now, the second step of the second aspect of the invention which is the reaction between the GA and the GADBA will be now explained.

The molar ratio of the GA (iv) based on the amount of the GADBA introduced into the reaction is usually from 0.2 to 4.0. Such values are suitable. When the molar ratio is less than 0.2, the synthesised amount of the GADMA tends to be very small and on the other hand when the molar ratio is more than 4.0, the synthesised amount of the GADMA does not increase and the amount of the GA which has to be separated via distillation after reaction increases which may not be economically interesting.

The reaction of the second step of the second aspect of the invention may usually be carried out without any solvent but the same solvents as shown in the first step of the second aspect of the invention can be optionally used.

The reaction of the second step of the second aspect of the invention progresses without any catalyst but industrially, in order to sufficiently increase the reaction speed, it is possible to use an acidic catalyst.

Catalysts that may be used are the same as those cited as examples in the first step reaction of the second aspect of the invention.

The amount of catalyst used, based on the amount of reaction solution is comprised in the same range as in the first step reaction of the second aspect of the invention. It is also possible to use the same catalyst.

The temperature of the second step reaction of the second aspect of the invention can be in the same range as the temperature of the first step reaction of the second aspect of the invention.

The reaction type used for the second step reaction of the second aspect of the invention can be the same as those given in example for the first step reaction of the second aspect of the invention.

After the reaction in the second step of the second aspect, in the case that a homogeneous catalyst is used in the reaction liquid, the catalyst is usually neutralised; in case of a solid catalyst, it is separated form the reaction solution via filtration to give a crude reaction solution.

Further, even if GADBA and GA remain due to the fact that the reaction is an equilibrium, needless to say that each of these component can be again reacted in the above-mentioned reaction to be converted into GADMA.

As described above, according to the second aspect of the invention, it is thus possible to obtain the target component GADMA from by-produced GADBA and GA.

Hereinafter, the third aspect of the invention will be now described.

In the second aspect of the present invention, after the end of the reaction of the first step of the second aspect, the GADMA which is the target compound is isolated via distillation from the crude reaction solution. However, in the process for isolating GADMA (iii), the determined conditions of the initial distillation whose aim is to remove low boiling-point component are an important characteristic of the invention which enables improving the yield of the GADMA. In other words, it is characterized in that the temperature of the solution of the bottom of the distillation column is in the range of 100° C. to 200° C. As a result, an improvement of the yield of the GADMA was achieved.

The reasons for such an improvement and operations for isolation via distillation will be more specifically explained hereafter.

After the end of the reaction of the first step of the second aspect of the invention, the crude solution which has been obtained after removing the catalyst is a mixture containing several kinds of compounds and it is considered that it is a chemically equilibrated solution. In addition to the target GADMA (iii), GA (iv) and GADBA (v) are also in the crude solution and each of them approximately in the same amount as the GADMA (iii).

When Y is an alkoxy group, the crude solution contains a by-produced alcohol which corresponds to the substituent group Y. This alcohol forms acetal compounds with GADMA (iii) and (GA (iv) which may be as some cases exemplified hereafter.

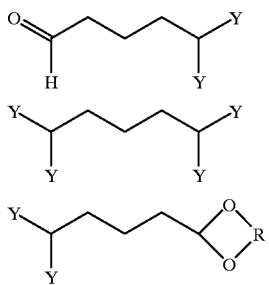

(wherein Y is a hydroxy group, an alkoxy group, an aryloxy group or an aralkyloxy group, R being a saturated or unsaturated hydrocarbon group having from 1 to 10 carbon atoms)

The reaction between the alcohol which corresponds to Y, GADMA (iii) and GA (iv) forms each kind of acetal compounds which coexist with the target GADMA. However, since the system is in a chemical equilibrium, an increased amount of each of these acetal compounds involves a decrease of the yield of GADMA which is a problem.

When using the technique disclosed in JP-A-49035383, GADMA are just obtained at an exceedingly low yield and further their purity is low. The reason of this phenomenon depends upon that fractionated distillation of GADMA and Y acetals which are formed from GADMA (iii) and GA (iv) and which correspond to the alcohol derived from Y group is difficult. Inventors of the present invention have discovered this phenomenon. (see Example III-1 and Comparative Example III-1 described in the specification of the present invention).

More specifically, after reaction, the crude reaction solution is heated, and at the same time, the alcohol which corresponds to Y and reaction solution of the first step is heated to 100° C. to 200° C. and after producing the target compound GADMA from by-products and during the synthesis thereof, alcohols corresponding to Y, phenols and other low boiling-point components are isolated via distillation. Accordingly, distillation separation of low boiling-point components can be carried out via distillation even at a temperature lower than 100° C. if this distillation is carried out immediately after heating.

According to the present invention, the yield of GADMA can be improved by degradation of Y acetals and their conversion into GADMA.

The above-mentioned operations can be carried out without removing the catalyst after the completion of the reaction. However, once the reaction is finished, the catalyst is preferably removed or neutralised and the resulting solution is then distilled to isolate GADMA. Such a process enables avoiding the progression of polymerisation, degradation or other side reactions which reduce the yield of GADMA and the purity thereof and also avoiding the apparition of problems regarding the increased viscosity of the solution of the bottom of the column which appear when catalyst remains in the distilled solution when carrying out the same operations as mentioned above.

When the catalyst is removed from the reaction solution after the completion of the reaction, the removal methods which can be used are separation via filtration when the catalyst is a solid such as ion-exchange resins or the like or neutralisation with an alkali compound or absorption by a basic solid when the catalyst forms a homogenous system such as sulphuric acid or the like.

It is to be noted that the end of the reaction can be monitored when YDP which is a starting material has disappeared and when the concentration of the synthesised GADMA becomes stable with lapse of time, The crude reaction solution from which the catalyst has been removed is distilled to isolate the target GADMA. This distillation can be a batch-type distillation or a continuous-type distillation using several distillation columns connected to one another.

In the distillation process, water, alcohols corresponding to Y, GA and diol are extracted at first from the system during the initial distillation operation. The characteristics of the present invention is in the range of the temperature of the solution of the bottom of the column which is from 100° C. to 200° C. and preferably from 130° C. to 180° C. When the temperature is maintained in this range, the above-mentioned Y acetals can be degraded. When the temperature of the solution of the bottom of the column is less than 100° C. the degradation reaction of Y acetals does not almost progress. On the other hand, when the temperature of the solution of the bottom of the column is more than 200° C., degradation of the target GADMA and side reactions such as polymerisation are accelerated which is not suitable.

It is to be noted that, when the temperature of the bottom of the column can be maintained in the above-described target range by adjusting the reduced pressure of the top of the column. Reduced pressures corresponding to a temperature of 100° C. to 200° C. are difficult to determine since they depend on the kind of the substituant group Y, in other words, they depend on the type of the alcohol corresponding to Y which is present in the solution of the bottom of the column. Further, since the internal pressure of the column is usually measured in the top thereof, the reduced pressures corresponding to a temperature of 100° C. to 200° C. also depend on the pressure loss inherent to the column. When Y is a methoxy group, an Oldershaw-type distillation column having 10 plates is used, the pressure at the top of the distillation column is approximately from 100 to 400 torr.

When the temperature of the solution of the bottom of the column is maintained in the above-mentioned range and when at the same time, alcohols synthesised from Y, phenols, water and the other low boiling-point components are distilled out, the extraction of alcohol corresponding to Y and degradation of Y acetals progresses at the same time. Finally, Y acetals disappear and are converted into corresponding GA or GADMA. Thus, the yield of GADMA is improved. Further, since the boiling point of GADMA is extremely near to the boiling point of some Y acetals, these acetals greatly decrease the purity of the product GADMA. However, as explained above, due to the degradation of Y acetals, a great decrease of the purity of GADMA can be largely avoided.

It is to be noted that, in the above-mentioned explanation and in the following Examples, although a batch-type distillation is mainly given as example. The present invention is not limited to such a batch distillation and a continuous distillation using several distillation columns connected to one another may also be used.

According to the third aspect of the invention, GADMA which is synthesised as a target compound can be recovered from by-products.

EXAMPLES

The present invention will be more specifically explained on the basis of the following Examples. However, the present invention is not limited to these Examples.

In the common parts, the first, the second and the third aspects of the present invention will be exemplified as follows.

The reaction apparatus is composed of an oil bath for heating and a three-neck flask equipped with a thermometer, a reflux condenser and a stirrer.

Cationic ion-exchange resin (Amberlite IR-124 (acidic type) produced by Organo CO, LTD) was used as catalyst.

The distillation apparatus was constituted of a distillation bottom flask, an Oldershaw-type distillation column having 10 plates, a condenser, a receiver and a reduced-pressure device.

Compositions of the reaction solution, distilled components and products were analysed via gas chromatography.

The first aspect of the invention will be now described by examples.

Example I-1

1,000 g of an aqueous solution containing 50% by weight of GA, 744 g of EG and 30 g of a catalyst were introduced into the flask and heated under stirring until the temperature of the reaction solution was equal to 90° C. The mixture was then maintained in this state for 3 hours.

After cooling, the crude solution was filtered to removed the catalyst and the filtrate was introduced in the bottom flask of the distillation column. Distillation was then carried out with a temperature in the range of 80° C. to 160° C., a reduced pressure of 300 torr to 30 torr; water and a small amount of EG were distilled out. A composition analysis of the solution remaining in the bottom of the distillation column (hereinafter designed as solution A) revealed that 1,089 g of this solution contained 899 g of GADBA.

1,000 g of an aqueous containing 50% by weight of GA was introduced in the bottom flask of the distillation column, and water and 29 g of GA were distilled out at 130° C. (temperature of the bottom flask) and under a reduced pressure of 400 torr. 469 g of the solution remaining in the bottom of the column (hereinafter designed as solution B) contained 459 g of GA having a water concentration of not more than 0.1% by weight.

1080 g of the solution A as obtained above, 465 g of the solution B obtained and 26 g of catalyst were introduced into the flask and heated under stirring until reaching the reaction temperature which was of 90° C. The mixture was kept under these conditions for 3 hours. After cooling, the crude solution was filtered to remove the catalyst and the filtrate was introduced in the bottom flask of the distillation column to carry out a reduced-pressure distillation. At 95° C. to 105° C. and under 30 torr, 237 g of a distilled fraction containing GA at a concentration of 82.2% by weight was obtained. Following the distillation, 674 g of a distilled fraction containing GADMA was obtained at a concentration of 94.5% by weight and at a temperature ranging from 119° C. to 122° C. and under a reduced pressure of 30 torr. The concentration of GADBA in 628 g of the solution remaining in the bottom of the column was of 73.9% by weight.

The yield of GADMA obtained in the product distilled fraction was of 44% by mole based on GA which was used as a starting material.

Comparative Example I-1

2,000 g of an aqueous solution containing 50% by weight of GA, 620 g of EG and 45 g of a catalyst were introduced into the flask and heated under stirring until the temperature of the reaction solution was equal to 90° C. The mixture was then maintained under these conditions for 3 hours.

After cooling, the crude solution was filtered to removed the catalyst and the filtrate was introduced in the bottom flask of an Oldershaw-type distillation column. Distillation was then carried out at a temperature in the range of 80° C. to 160° C. and under a reduced pressure of 300 torr to 30 torr; 1,560 g of a distilled solution (concentration in GA of 26.4%) containing GA and water was obtained. Following the distillation, 179 g of a product fraction containing 88.5% by weight of GADMA were obtained at 173° C. under a reduced pressure of 30 torr. 875 g of the solution remaining in the bottom of the column contained 21 g of GADMA and 757 g of GADBA.

The yield of GADMA obtained in the product distilled fraction was of 11% by mole based on GA which was used as a starting material.

According to the first aspect of the invention, it is possible to produce industrially and in an advantageous manner dialdehyde monoacetal (iii).

Hereinafter, the second aspect of the invention will be now described.

Example II-1

635 g of MDP, 345 g of EG and 17 g of a catalyst were introduced into the flask and heated under stirring until the temperature of the reaction solution was equal to 90° C. The mixture was then maintained in this state for 3 hours.

After cooling, the crude solution was filtered to remove the catalyst and the filtrate was introduced in the bottom flask of the distillation column for a reduced-pressure distillation. The initial fraction of methanol was distilled out when the temperature of the bottom solution was of 130° C., the pressure of the top of the column between 170 torr and 400 torr and the temperature of the top of the column in the range of 35° C. to 56° C. The temperature of the solution of the bottom was then increased until 130° C. to 142° C., the temperature of the top of the column was then from 95° C. to 105° C. and the pressure thereof of 30 torr. Under such conditions, 108 g of a distilled solution containing 81.4% of GA was obtained and the temperature of the bottom solution was further increased until 142° C. to 168° C., the temperature of the top of the column being 119° C. to 124° C. and the pressure thereof of 30 torr. Under such conditions, 318 g of a distilled solution containing 94.3% of GADMA was then obtained. 329 g of the solution remaining in the bottom of the column contained 79.4% of GADBA. (the yield of GADMA was of 37% based on MDP).

1000 g of the distilled fraction of GA obtained as above-mentioned (equivalent to 81 g of GA), 315 g of the solution remaining in the bottom of the distillation column (equivalent to 250 g of GADBA) and 7 g of the catalyst were introduced into a flask and reacted for 3 hours at 90° C. It was verified by an analysis of the crude reaction solution that 151 g of GADMA have been produced. Further, the concentration of EG in the crude reaction solution was not more than 0.1%.

After filtration of the catalyst, the resulting filtrate was submitted to a distillation as explained above for the first reaction. As in the first reaction, 155 g of a product fraction which contained 94.5% of GADMA were obtained together with a distilled fraction of GA, a solution remaining in the bottom of the column and containing GADBA at a temperature of from 119° C. to 124° C. and under 30 torr (the yield of GADMA was of 19% based on the amount of MDP which was introduced in the first reaction, the total yield including the yield in the first reaction was of 56%)

Comparative Example II-1

322 g of the bottom solution which contains 77.1% of GADBA and which was obtained after carrying out a first reaction and a distillation according to Example II-1 (equivalent to 248 g of GADBA), 62 g of water and 7 g of a catalyst were introduced into a flask and reacted for 3 hours at 90° C. It has been checked by a composition analysis of the crude solution that 61 g of GADMA have been produced. Further, the concentration of EG in the crude reaction solution was of 13.2%.

The catalyst was filtered out and a distillation according to Example II-1 was then carried out with the resulting filtrate. However, it was not possible to obtain a distilled fraction containing GADMA. 298 g of the solution remaining in the bottom of the distillation column contained 81% of GADBA (equivalent to 241 g of GADBA) and thus it has been checked that almost the total amount of GADMA produced during reaction has been returned into GADBA during the distillation process.

According to the second aspect of the invention, it is possible when reacting 2-alkoxy-3, 4-dihydro-2H-pyran (i) and the diol (ii) to obtain GADMA and to isolate GADMA obtained at a high yield via reacting GADBA which are by produced during the former reaction with GA which are another by-product. This can be carried out without any problems of reverse conversion of GADMA into GADBA during separation, whereby GADMA can be isolated at a high yield.

Hereinafter, the third aspect of the invention will be now explained.

Example III-1

6359 of MDP (5.57 mole), 345 g of EG (5.57 mole) and 17 g of a catalyst were introduced into a flask and heated under stirring until reaching the reaction temperature of 90° C. The mixture was maintained in such conditions for three hours. After cooling, the catalyst was filtered out of the crude reaction solution and the composition of the resulting filtrate was analysed. This filtrate contained 71.8 g of methanol (2.24 mole), 7.5 g of EG (0.12 mole), 7.5 g of MDP (0.07 mole), 102.6 g of GA (1.03 mole), 182.2 g of GADMA (1.27 mole), 223.3 g of GADBA (1.19 mole) and 384.8 g of other by-products. Further, if stoichiometry is applied, although the number of mole of methanol produced (5.57) should correspond to the amount of MDP (starting material) which has reacted, since in reality this amount is rather little, it is clear that the methoxy groups has been partially converted into other groups.

This filtrate was introduced into the bottom of a distillation column and distilled under a pressure of the top of the column of 400 torr to 170 torr, at a temperature of the bottom of the column of from 130° C. to 132° C., thereby, 138.9 g of a distilled fraction containing 133.0 g (4.16 mol) of methanol was then obtained.

Subsequently, 132.9 g of a distilled fraction containing 93.9 g (0.939 mole) of GA was obtained under a pressure of the top of the column of 30 torr and at a temperature of the bottom of the column of from 130° C. to 142° C. Subsequently further, 317.6 g of a distilled product fraction containing 301.5 g (2.09 mole) of GADMA was obtained under a pressure of the top of the column of 30 torr and at a temperature of the bottom of the column of from 142° C. to 168° C. 329 g of the solution remaining in the bottom of the column contained 261.3 g (1.39 mole) of GADBA. Moreover, the purity of the product was of 94.9% by weight and the yield of GADMA based on the amount of MDP was of 37.5% by mole.

According to the above-mentioned results, it has been proved that during the distillation of the crude reaction solution, methanol is produced and at the same time the amount of GADMA increases.

Comparative Example III-1

As in Example III-1, 635 g (5.57 mole) of MDP and 345 g (5.57 mole) of EG were reacted in the presence of 17 g of a catalyst.

The crude reaction solution was filtered and the resulting filtrate contained 73.6 g (2.30 mole) of methanol, 7.2 g (0.12 mole) of EG, 7.1 g (0.06 mole) of MDP, 104.0 g (1.04 mole) of GA, 186.7 g (1.30 mole) of GADMA, 228.9 g (1.22 mole) of GADBA and 373.5 g of other by-products.

This filtrate was introduced into the bottom of a distillation column and 101.39 g of a distilled fraction containing 67.7 g (2.12 moles) of methanol was obtained under a pressure of the top of the column of 30 torr to 3 torr and at a temperature of the bottom of the column of from 60° C. to 70° C. The distillation was followed to obtain 173.9 g of a distilled fraction containing 95.6 g (0.956 mole) of GA under a pressure of the top of the column of 3 torr and at a temperature of the bottom of the column of from 70° C. to 89° C. By further following the distillation, 115.8 g of a distilled fraction containing 104.2 g (0.724 mole) of GADMA was obtained under a pressure of the top of the column of 3 torr and at a temperature of the bottom of the column of from 89° C. to 117° C. 231.3 g (1.23 mole) of GADBA was contained in 588.9 g of the solution remaining in the bottom of the column. Further, the purity of the product was of 90.0% and the yield of GADMA based on the amount of MDP was of 13.0 by mole.

According to the third aspect of the invention, when isolating GADMA via distillation of a crude reaction solution obtained from the reaction between YDP and diol, it is possible by setting the temperature of the bottom of the column in the range of 100° C. to 200° C. during the initial distillation to reduce the production of Y acetals an other undesired acetals and thus to improve the yield of the target GADMA.

What is claimed is:

1. A method of producing a dialdehyde monoacetal (III) from a dialdehyde (I) and a diol (II) characterised in that it comprises:

a first step where said dialdehyde (I) and said diol(II) are reacted to obtain a dialdehyde bisacetal (IV), the mole amount of said diol(s) (II) being at least twice amount of said dialdehyde (I); and a second step where said dialdehyde bisacetal (IV) is reacted with said dialdehyde (I); said dialdehyde (I), diol (II), dialdehyde monoacetal (III) and dialdehyde bisacetal (IV) being shown in the following Formulae (I) to (III)

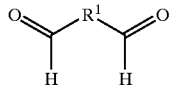
(I)

wherein $R^1$ is a hydrocarbon group

HO—$R^2$—OH   (II)

wherein $R^2$ is a hydrocarbon group

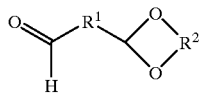
(III)

(wherein $R^1$ and $R^2$ are the same as in Formulae (I) and (II) respectively

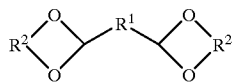
(IV)

wherein $R^1$ and $R^2$ are the same as in Formulae (I) and (II) respectively.

2. The method for producing a dialdehyde monoacetal of claim 1, wherein the first step and/or the second step are carried out in the presence of an acidic catalyst.

3. The method for producing dialdehyde monoacetal(s) of claim 1, wherein said dialdehyde (I) used in the reaction with dialdehyde bisacetal(s) (IV) is anhydrous.

4. A method for producing a glutaraldehyde monoacetal via reacting a 2-Y-3, 4-dihydro-2H-pyran or a ring-substituted derivative thereof as shown in General Formula (i) with a diol as shown in General Formula (ii) to obtain glutaraldehyde monoacetal as shown in General Formula (iii), characterised in that said glutaraldehyde monoacetal (iii) is produced in a second step reaction wherein said glutaraldehyde (iv) which is a by-product of the first step reaction is reacted with glutaraldehyde bisacetal (v) which is another by-product of the same reaction; 2-Y-3, 4-dihydro-2H-pyran, diol (ii), glutaraldehyde monoacetal (iii), glutaraldehyde (iv) and glutaraldehyde bisacetal (v) being as shown in the following General Formulae:

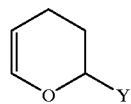
(i)

wherein Y is a hydroxy group, an alkoxy group, an aryloxy group or an aralkyloxy group HO—R—OH   (ii)

wherein R is a divalent saturated or unsaturated hydrocarbon group having from 1 to 10 carbon atoms

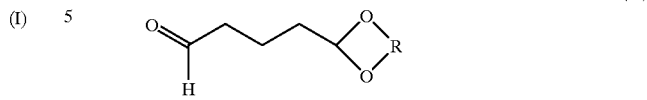
(iii)

wherein R is as defined in General Formula (ii)

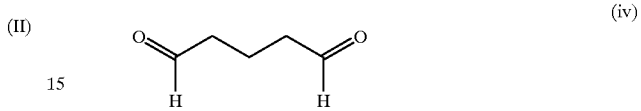
(iv)

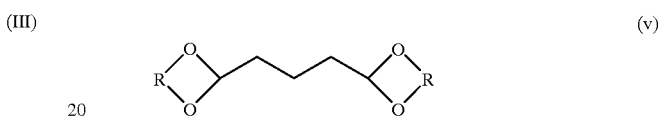
(v)

wherein R is as defined in General Formula (ii).

5. The method of producing a glutaraldehyde monoacetal of claim 4, wherein in the process for isolating glutaraldehyde monoacetal via distillation of the crude reaction solution of the first step, the initial distillation operation for removing low boiling-point components is carried out while maintaining the temperature of the solution in the bottom flask of the distillation column in the range of 100° C. to 200° C.

6. The method for producing a glutaraldehyde monoacetal of claim 4, wherein after the end of the first step reaction, the crude solution is heated until a temperature comprised between 100° C. and 200° C., glutaraldehyde monoacetal (iii) being produced from by-products and the low boiling-point components produced from the substituant group Y being distilled out during the production of said glutaraldehyde monoacteal (iii).

7. The method of producing a glutaraldehyde monoacetal of claim 4, wherein said 2-Y-3, 4-dihydro-2H-pyran is 2-methoxy-3, 4-dihydro-2H-pyran and said diol is ethylene glycol.

8. The method of producing a glutaraldehyde monoacetal of claim 7, wherein a crude reaction solution in said first step is separated into a fraction primarily containing glutaraldehyde and a fraction primarily containing glutaraldehyde monoacetal via distillation.

9. The method for producing a glutaraldehyde monoacetal of claim 8, wherein the separation of the fraction primarily containing glutaraldehyde is carried out at a temperature of the solution of the bottom flask of the column of 130° C. to 142° C. and under a pressure of the top of the column of from 25 torr to 35 torr and at a temperature of the top of the column of from 95° C. to 119° C.

10. The method for producing a glutaraldehyde monoacetal of claim 8 or 9, wherein the separation of the fraction primarily containing glutaraldehyde monoacetal is carried out at a temperature of the solution of the bottom of the column of from 142° C. to 168° C. and under a pressure of the top of the column of from 25 torr to 35 torr and at a temperature of the top of the column of from 119° C. to 124° C.

* * * * *